United States Patent
Shantz et al.

(10) Patent No.: US 6,960,349 B2
(45) Date of Patent: Nov. 1, 2005

(54) PRE-MOISTENED WIPE WITH LOTION TO IMPROVE DISPENSING

(75) Inventors: Barry Shantz, Cincinnati, OH (US); Jane L. Bavely, Cincinnati, OH (US); Marc F. Richards, Corinth, KY (US); George Deckner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/918,223

(22) Filed: Jul. 30, 2001

(65) Prior Publication Data

US 2001/0055609 A1 Dec. 27, 2001

Related U.S. Application Data

(63) Continuation of application No. 09/344,695, filed on Jun. 25, 1999, now abandoned, which is a continuation-in-part of application No. 09/281,886, filed on Mar. 31, 1999, now abandoned.

(51) Int. Cl.[7] ........................... A01N 25/34; A61K 7/06; A61K 7/08
(52) U.S. Cl. .................. 424/402; 424/70.11; 424/7.19; 424/70.31
(58) Field of Search ........................... 424/70.11, 70.19, 424/70.31, 402

(56) References Cited

U.S. PATENT DOCUMENTS

| | | | | |
|---|---|---|---|---|
| 5,332,118 A | * | 7/1994 | Muckenfuhs | 221/48 |
| 5,436,007 A | | 7/1995 | Hartung et al. | |
| 5,567,427 A | | 10/1996 | Papadakis | |
| 5,618,850 A | * | 4/1997 | Coury et al. | 514/772.2 |
| 5,648,083 A | * | 7/1997 | Blieszner et al. | 424/402 |
| 5,704,471 A | | 1/1998 | Yamada | |
| 5,863,943 A | | 1/1999 | Groh | |
| 5,871,763 A | * | 2/1999 | Luu et al. | 424/402 |
| 5,891,008 A | * | 4/1999 | Bavely et al. | 493/405 |
| 5,919,471 A | | 7/1999 | Saferstein et al. | |
| 6,361,784 B1 | * | 3/2002 | Brennan et al. | 424/402 |

FOREIGN PATENT DOCUMENTS

| | | |
|---|---|---|
| EP | 0 161 425 A2 | 11/1985 |
| EP | 0 613 675 A1 | 9/1994 |
| EP | 0 870 496 A2 | 10/1998 |
| WO | WO 97/22544 | 6/1997 |
| WO | WO 99/11553 | 3/1999 |
| WO | WO 99/25318 * 5/1999 | ............ A61K/7/50 |

OTHER PUBLICATIONS

Homebest Premium Baby Wipes, on sale in the US prior to Aug. 31, 1999.

* cited by examiner

Primary Examiner—Thurman K. Page
Assistant Examiner—S. Tran
(74) Attorney, Agent, or Firm—Roddy M. Bullock; Ian S. Robinson; Matthew P. Fitzpatrick (57) ABSTRACT

A lotion suitable for use in a disposable wiping article is disclosed. The lotion can be used to wet pre-moistened wet wipes, and is particularly suited for use in pop-up dispensing systems of disposable wet wipes, such as baby wipes. The lotion provides for improved reliability of pop-up dispensing while maintaining adequate wet impression. The lotion is an aqueous solution comprising a surfactant selected from the group consisting of phosphate-quaternary amine compounds and non-ionic surfactants, and effective amounts of a second ingredient selected from the group consisting of non-cellulosic organic water soluble polymers and alkoxylated alcohols. Other ingredients such as preservatives and fragrances can also be included in the lotion.

7 Claims, 4 Drawing Sheets

PRE-MOISTENED WIPE WITH LOTION TO IMPROVE DISPENSING

This application is a continuation of Ser. No. 09/344,695 filed Jun. 25, 1999 abandoned, which is a Con-In-Part of application Ser. No. 09/281,886 filed Mar. 31, 1999 now abandoned.

FIELD OF THE INVENTION

The present invention is related to disposable wiping articles, and more particularly to pre-moistened wipes suitable for pop-up dispensing.

BACKGROUND OF THE INVENTION

Pre-moistened cleansing wipes are well known, and are referred to as wet wipes, towelettes, and the like. Pre-moistened wipes include a substrate, such as a nonwoven web, pre-moistened with a lotion. The lotion can be an aqueous lotion, and typically includes one or more surface active materials (surfactants). The lotion can also include preservative and fragrance ingredients.

Pre-moistened wipes find use at home or away from home, especially with the cleansing of children and infants. For example, wipes are often used to clean an infant's skin during a diaper change. As well, pre-moistened wipes find use among adults, typically in conjunction with the use of incontinence articles. Other uses of pre-moistened wipes include general cleaning tasks where soap, cloths, and running water may be unavailable, unsuitable, or inconvenient for a particular task. In almost all instances, pre-moistened wipes are provided as folded, stacked, sheets of disposable wipes, each wipe meant for one-time use. Thus, pre-moistened wipes are often referred to as disposable wet wipes.

There are two basic types of containers for providing stacked sheets of pre-moistened wipes to the user. In one container type, often referred to as a "reach in" container, the premoistened wipes are in a folded, stacked arrangement of discreet sheets. This configuration permits one towel at a time to be exposed to the user, who "reaches in" and extracts the topmost wipe from the container. The remaining wipes remain in their stacked, folded configuration. Reach in containers often have a tub-like configuration (a rigid container) or a soft, generally rectangular package configuration and usually have a recloseable lid or cover to protect the remaining wipes from prematurely drying out.

One drawback to "reach in" containers is that wipes that are merely folded and stacked one on top of the other provide no means of conveniently providing the user with an edge or other portion to grasp for removal. The user must find and grasp the leading edge of the topmost wipe, which often is difficult to do. Thus, the consumer must try to find a free edge of the top wipe, and peel the wipe free from the remaining stack of wipes. This is often a time consuming and frustrating procedure, and can distract from the task at hand. Another drawback that reach in dispensing arrangements do not provide for simple, single dispensing of consecutive sheets. For example, as one sheet is removed, the next sheet remains in its folded, stacked configuration, requiring the user to reach into the tub or container to remove the next sheet. This can become inconvenient as the stack of wipes gets smaller, thereby requiring the user to reach further into the tub or container.

A second container type is commonly referred to as a "pop up" dispenser, wherein the trailing edge of a wipe being extracted from the package first draws the leading edge of the next wipe through an aperture or opening. As the first wipe exits the container, it is separated from the leading edge of the next wipe, leaving the leading edge of the next wipe held in a readily accessible position by the edges of the aperture. In one pop-up arrangement, discreet, folded wipes are interleaved in the stacked configuration. The wipes are interleaved (interfolded) such that they have overlapping edge portions which adhere to one another. The adhesion forces in the overlapping region supply the necessary force to permit one wipe to pull the leading edge of the next wipe through the container opening before separation of the respective overlapping regions occurs.

Pop-up dispensing is preferred by consumers because with each wipe used, when working properly, the leading edge of the next wipe is presented for easy grasping. The leading edge of the next wipe can be conveniently tucked into a suitable space in the top of the container prior to closing a cover which keeps the leading edge of the wipe from drying out. Upon occasion for use, the user simply opens the cover, grasps the leading edge of the wipe and pulls the wipe through the dispensing opening, which in turn pulls the leading edge of the next consecutive wipe through the opening.

Although consumer preferred, there are drawbacks to pop-up dispensing. The major drawback is dispensing reliability, i.e., the ability of the dispensing system to reliably dispense one sheet per pull, while leaving a portion of the leading edge of the next wipe accessible. The various problems associated with pop-up dispensing impact the design of the fold patterns, container configurations, opening size and shape, as well as overall wipe design. The problems associated with pop-up dispensing reliability include chaining, fallback, liftoff, and long edges.

Chaining occurs when product separation does not occur as one sheet is removed, and thus multiple sheets are withdrawn in a continuous "chain" of product. Even if it is only a two wipe "chain" the result is unwanted wipes being drawn from the container.

Fall back occurs when the wipe sheets separate prematurely before the next sheet is drawn into the dispensing opening. The next sheet thus falls back inside the container, and the user does not have a portion of the next wipe available for grasping.

Liftoff occurs when, in an attempt to extract the next wipe, the entire tub or container lifts into the air. The user must then use two hands to remove the desired wipe. If only one hand is available, the user must yank, jerk, or otherwise try to free the desired wipe from the container. Of course, this causes unnecessary aggravation to the consumer, who is often engaged in the unpleasant task of changing an infant's diapers at the time.

Long edges occur when too much of the leading edge of the next wipe is exposed through the dispensing opening after extracting the previous wipe. If a long edge is exposed, it can cause problems closing the cover over the dispensing opening because there is too much wipe to tuck into the designated area. Also, having long edges extend out of the dispensing opening causes a larger portion of the wipe to be more prone to prematurely drying out, thereby being of little value as a wet wipe to the consumer.

The reliability of pop-up dispensing, i.e., the minimizing of the above-mentioned drawbacks, can be impacted by the complex interaction of product moisture loading, dispensing orifice size and/or shape, extent of product overlap, compression during manufacture, and substrate properties. Efforts at improving pop-up dispensing have been focused primarily on improvements to containers, dispensing openings, wipe edge modifications, and interleaving configurations. However, due to the complex interaction of the various design parameters, there remains a need to provide reliable pop-up dispensing of pre-moistened wipes.

Accordingly it would be desirable to provide a pre-moistened wipe suitable for use in a pop-up container having reliable dispensing properties.

Additionally, it would be desirable to provide a pre-moistened wipe exhibiting reliable pop-up dispensing, and which also exhibits sufficient wetness perception levels for consumer acceptance.

Further, it would be desirable to provide a folded, stacked, interleaved sheets of pre-moistened wipes suitable for reliable pop-up dispensing.

Further, it would be desirable to provide a pop-up dispensing system for wet wipes which results in improved ease of dispensation and separation of a single wipe from the wet wipe stack and easy recognition of the location and ease of grasping the leading edge of each subsequent wipe.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

SUMMARY OF THE INVENTION

A lotion suitable for use in a disposable wiping article is disclosed. The lotion can be used to wet pre-moistened wet wipes, and is particularly suited for use in pop-up dispensing systems of disposable wet wipes, such as baby wipes. The lotion provides for improved reliability of pop-up dispensing while maintaining adequate wet impression. The lotion is an aqueous solution comprising a surfactant selected from the group consisting of phosphate-quaternary amine compounds and non-ionic surfactants, and effective amounts of a second ingredient selected from the group consisting of non-cellulosic organic water soluble polymers and alkoxylated alcohols. Other ingredients such as preservatives and fragrances can also be included in the lotion.

DETAILED DESCRIPTION OF THE INVENTION

The pre-moistened wipes of the present invention comprise a substrate moistened with a lotion. The substrate can comprise a woven or nonwoven web formed of natural fibers, synthetic fibers, or combinations thereof suitable for use as a pre-moistened wipe such as a wet wipe. The lotion comprises an aqueous solution and can include a surfactant and/or a cosurfactant/foam building agent/emulsifier and/or a non-cellulosic water soluble organic polymer.

The term "aqueous solution" as used herein refers to a solution that is at least 50 percent by weight water.

The term "pre-moistened wipe" as used herein refers to a wipe which includes a substrate which is moistened, such as by wetting the substrate with a liquid composition, prior to use by the consumer. In particular, "pre-moistened wipe" refers to wipes having a substrate which is moistened prior to packaging, such as in a generally moisture impervious container or wrapper.

Such pre-moistened wipes, which can also be referred to as "wet wipes" and "towelettes", are suitable for use in cleaning male and female babies, as well as adults of all ages. Such wipes also include articles used for application of substances to the body, including but not limited to application of make-up, skin conditioners, ointments, and medications. Such wipes can also include such articles used for cleaning or grooming of pets, and articles used for general cleansing of surfaces and objects, such as household kitchen and bathroom surfaces, eyeglasses, exercise and athletic equipment, automotive surfaces, and the like.

As used herein, the term "weight percent" or "percent by weight" is meant to refer to the quantity by weight of a component in the lotion of the wipe as a percentage of the total weight of the lotion.

As used herein, the term "water soluble" means that a component is soluble or otherwise dispersible (such as to provide a micellar solution) in water at a level of at least about 0.25 percent by weight at 25 degrees Centigrade.

As used herein, the term "surfactant" refers to materials which preferably orient toward an interface, classes of surfactants including nonionic surfactants, anionic surfactants, cationic surfactants, amphoteric surfactants, zwitterionic surfactants, and mixtures thereof.

As used herein, the terms "emulsifier" or "solubilizer" refer to a component that reduces the tendency of one or more other components in a lotion composition to phase separate from the lotion.

As used herein, the term "cosurfactant" means a component that can act as either a surfactant or an emulsifier/solubilizer.

As used herein the term "organic water soluble polymer" means an organic compound formed by the joining of smaller molecules, referred to as monomers. The term is generally used to refer either to a macromolecule made up of a large number of monomers linked by covalent bonds, e.g., polypeptides, nucleic acids, polysaccharides, and plastics, or to a protein made up of several subunits linked by covalent or noncovalent bonds, e.g., hemoglobin or lgM immunoglobulin.

As disclosed herein, it has been found that pop-up dispensing reliability is significantly impacted by the lotion applied to the pre-moistened wipe. While other factors, such as substrate type, dispensing opening, stacking configuration and wipe edge modifications can and do play an important role, the lotion of the present invention has been found to be the primary factor in determining pop-up dispensing reliability. In addition to providing for increased reliability in a given configuration of pre-moistened wipes and container arrangement, the lotion components can be adjusted to exhibit adequate perceived wetness by the consumer.

The lotion of the present invention, as well as preferred substrates, dispensing openings, and stacking arrangements of the present invention are disclosed below with reference to the FIGURES for purposes of illustrating its features and advantages. The present invention is described in detail below in relation to preferred embodiments and examples of beneficial lotions.

Figure 1:
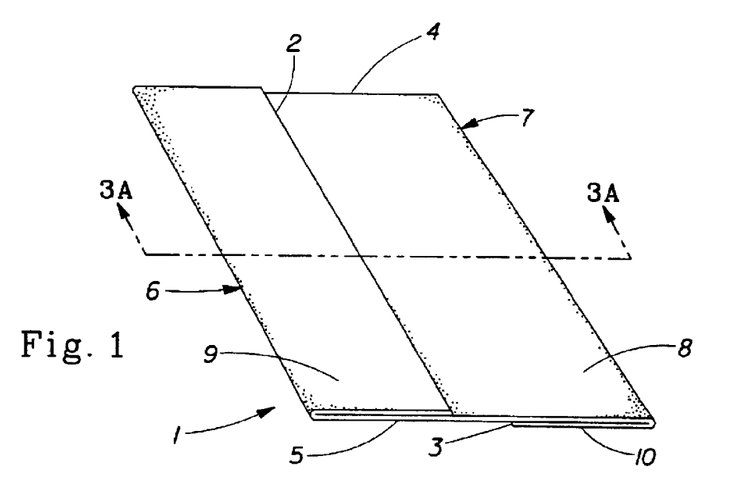
FIG. 1 is a perspective view of a Z-folded pre-moistened wipe of the present invention.
Figure 2:
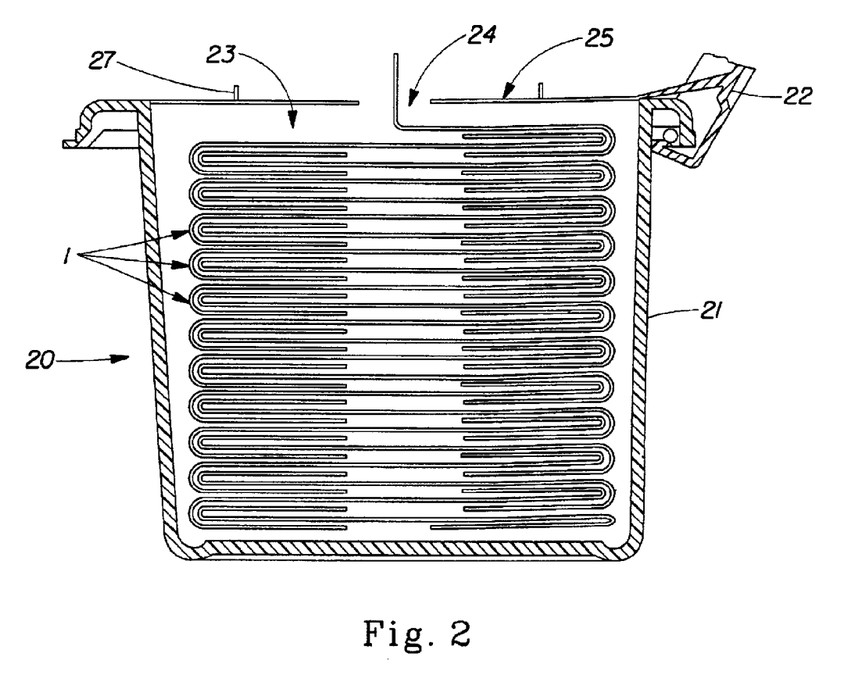
FIG. 2 is a cross-sectional schematic illustration of a stack of folded and interleaved wet wipes in a dispensing container.
Figure 3A:
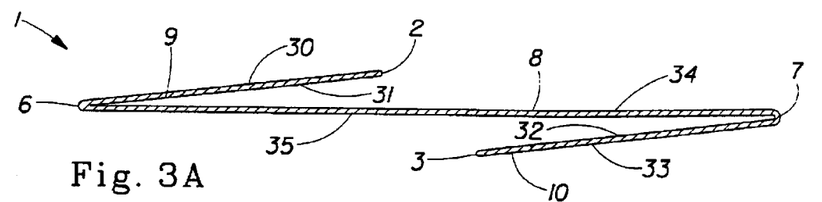
FIG. 3A is a cross-sectional schematic illustration taken along line X—X in FIG. 1 showing a wipe having a leading edge panel, a central panel and a trailing edge panel and folded in a Z-fold configuration.

FIG. 1 provides a perspective view of a single folded pre-moistened wipe 1 of the present invention. Wipe 1 can be folded in any of various known folding patterns, such as C-folding, but is preferably Z-folded as shown in FIGS. 1 and 3. A Z-folded configuration enables a folded stack of wipes to be interleaved with overlapping portions as shown in FIG. 2.

As shown in FIG. 1, each folded wipe 1 extends lengthwise from a first, leading end edge 2, to a second, trailing end edge 3. Thus, in a preferred embodiment, each wipe 1 has at least two folds thereby providing three panels. As used herein, a panel is a portion of a wipe extending between two folds, or between a fold and edge end.

The first panel fold 6 can be generally parallel to the leading edge 2, and generally perpendicular to side edges 4, and 5. The first panel fold 6 is spaced lengthwise from the leading edge 2 to provide a leading edge panel 9 extending between the first panel fold 6 and the leading edge 2. The second panel fold 7 is generally parallel to, and spaced lengthwise from, the first panel fold 6, thereby providing a central panel 8 joined to the leading edge panel 9, at the first panel fold 6, and extending between the first panel fold 6 and the second panel fold 7. The trailing edge panel 10 is joined to the central panel 8 at the second panel fold 7, and extends between the second panel fold 7 and the trailing edge 3.

According to the preferred embodiment of the dispensing system of the present invention, the wipes are folded at the first and second panel folds 6 and 7, to provide the corresponding leading edge panel, central panel, and trailing edge panels 8, 9, and 10. The wipes can thus be folded into a number of configurations prior to interleaving. This is clearly demonstrated with reference to the respective surfaces of each of the panels as indicated in FIG. 3.

In FIG. 3A, each wipe has a first upper surface leading edge panel 30, a second lower surface leading edge panel 31, a first upper surface trailing edge panel 32, a second lower surface trailing edge panel 33, a first upper surface central panel 34 and a second lower surface central panel 35. The leading edge panel and the trailing edge panel may thus be provided by the first panel fold and the second panel fold respectively such that the panel rests on the upper facing surface of the central panel or the lower facing surface of the central panel.

As shown in FIGS. 1 and 3A, the leading edge panel 9 is adjacent to and overlies a portion of the upper facing surface of the central panel 8 and the trailing edge panel is adjacent to and underlies a portion of the lower facing surface of the central panel 8 thereby providing a so-called "reversed Z-folded" wipe. Alternatively, the wipes may be folded so as to provide a Z-fold configuration.

In yet another embodiment, both the leading edge panel and the trailing edge panel of each wipe may be folded such that they are both adjacent and overlie a portion of the upper surface of the central panel, being folded into a so-called "C-fold" configuration.

Figure 3B:
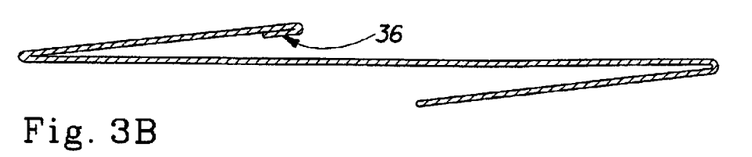
FIG. 3B is a cross-sectional schematic illustration of a folded wipe having a lip on the leading edge panel.

Furthermore, in addition to the leading edge panel, central panel and trailing edge panel described herein above, each wipe may also have further additional panels. In particular, the leading edge panel and or the trailing edge panel may also be provided with an additional fold so as to provide a leading edge panel lip 36 or a trailing edge panel lip as illustrated in FIG. 3b. Such a lip is formed by providing the leading edge panel or the trailing edge panel with a panel lip fold which is adjacent to and spaced from the leading or trailing edge of the folded substrate to provide a lip extending between the panel lip fold and the end edge. The panel lip fold may be folded onto the lower surface of the leading edge panel such that the leading end edge is below the leading edge end panel. This configuration is particularly beneficial in facilitating grasping of the edge. Alternatively, the leading edge panel may be folded such that the leading end edge rests on the upper surface of the leading edge panel. The lip may also be positioned on the upper or lower surface of the trailing edge panel. The lip typically extends from the leading or trailing edge from between 4 cm to 0.1 cm, preferably from 2 cm to 0.25 cm to the leading edge panel lip fold or the trailing edge panel lip fold.

According to the present invention, the overall dimensions of the substrate material and the panels thereof is dependent on the intended application of the wipe and can be selected accordingly. Preferably the ratio of the lengths of the leading edge panel to central panel to trailing edge panel is from 1:2:1 to 1:5:1 and most preferably the ratio is 1:3:1. More preferably the ratio of the lengths of the panels of the wipes of the first and second assembly of wipes are identical and most preferably the leading and trailing edge panels are both approximately one quarter the total length of the wipe. In one non limiting, illustrative example wherein the wipe may be utilized as a baby wipe, each folded wipe 1 can have an unfolded length of from 10 cm to 30 cm as measured lengthwise from the leading end edge 2 to the trailing end edge 3. For each folded wipe 1, the spacing between the first panel fold 6 and the second panel fold 7 can be from 2 cm to 7 cm, while the lengths of the leading edge panel 9 and trailing edge panel 10 can be from 2 cm to 7 cm. In a preferred embodiment the spacing between the first panel fold 6 and the leading end edge 2 is more preferably from 3 cm to 6 cm, and even more preferably between about 3 cm and 5 cm. The spacing between the first panel fold 6 and the second panel fold is more preferably from 3 cm to 12 cm, and even more preferably between about 10 cm and 12 cm. The spacing between the second panel fold 7 and the trailing edge is more preferably from 3 cm to 6 cm, and even more preferably between about 3 cm and 5 cm.

According to the present invention and with reference to the embodiments illustrated in FIGS. 4A, 4B, 4C and 4D, an essential feature of the stacking configuration is that each of the first assembly of folded wipes 40 are interleaved with each of the second assembly of folded wipes 50.

For example wipe x of the second assembly of wipes is folded in a Z fold and interleaved between a reverse Z folded wipe x of the first assembly of wipes. Similarly wipe y of the first assembly of wipes is interleaved between wipe x of the second assembly of wipes and wipe y of the first assembly of wipes is interleaved with wipe y of the second assembly of wipes and so on. In this manner, commencing with the second assembly wipe x, at least a portion of said central panel 52x and at least a portion of said leading edge panel 51x of each of said second assembly of wipes 50 are interleaved with wipe x of the first assembly of wipes between at least a portion of said trailing edge panel 43x and at least a portion of said central panel 42x of each of said first assembly of wipes 40. Similarly, at least a portion of said central panel 42y and at least a portion of said leading edge panel 41y of each of said first assembly of wipes 40, are interleaved between at least a portion of said trailing edge panel 53x and at least a portion of said central panel 52x of each of said second assembly of wipes 50.

According to the present invention another essential feature of the stacking configuration is related to the relative lengths of the panels of each of the wipes of the first and second assemblies. Accordingly, it has been found that the length of the leading edge panel or the trailing edge panel of each wipe for example wipes x of said first assembly of wipes, is no more than 50% of the length of the corresponding central panel. Similarly, the length of the leading edge panel or said trailing edge panel of each wipe of said second assembly of wipes, is no more than 50% the length of the corresponding central panel. Hence, the leading and trailing edge panels of each of the first and second assemblies of wipes may be of any length provided that the sum of the length of the leading edge panel and the length of the trailing edge panel of any wipe is not greater than the length of the corresponding central panel of the wipe. Preferably however, the lengths of the panels of all of the wipes in each assembly and more preferably the corresponding panels in both first and second assemblies are of substantially identical dimensions.

Wet wipes stacked as described herein above result in superior dispensation than wipes stacked according to the prior art. Whilst not wishing to be bound by theory it has been found that the improved dispensing is related to the combination of the specific interleaved folding configuration between the first and second assemblies of wipes and the specific area of overlap between the panels of the wipes.

By the utilization of the herein above described interleaving configuration the removal of the uppermost wipe, for example wipe x of the first assembly, from the interleaved stack will cause the agitation of the leading edge panel and central panel of the adjacent wipe x of the second assembly from the stack. This thereby facilitates the identification of the location of the leading edge of the adjacent wipe to the consumer, in particular as the leading edge of the adjacent wipe whilst agitated tends to remain positioned upon the central panel thereby providing a thickened portion for the consumer to grasp. Furthermore, it has been found that the area of overlap between the leading edge panel of the adjacent wipe (i.e. wipe x of the second assembly of wipes) and the central panel or trailing edge panel of the uppermost wipe, (i.e. wipe x of the first assembly of wipes) ensures that the required amount of length of the substrate material of the wipe x of the second assembly is raised and separated from the stack. The area of overlap between the central panel of the adjacent wipe (x of the second assembly) and the trailing edge panel or the central panel of the uppermost wipe (x of first assembly) appear to be of lesser importance. Hence, the positioning of the first and second panel folds and the relative lengths of the leading and trailing edge panels to the central panel is of critical importance. However, the improved dispensation provided by the present invention may also involve other effects and interactions in addition to or instead of the hypothesis given, and hence no reliance should be placed thereon.

Figures 4A, 4B:
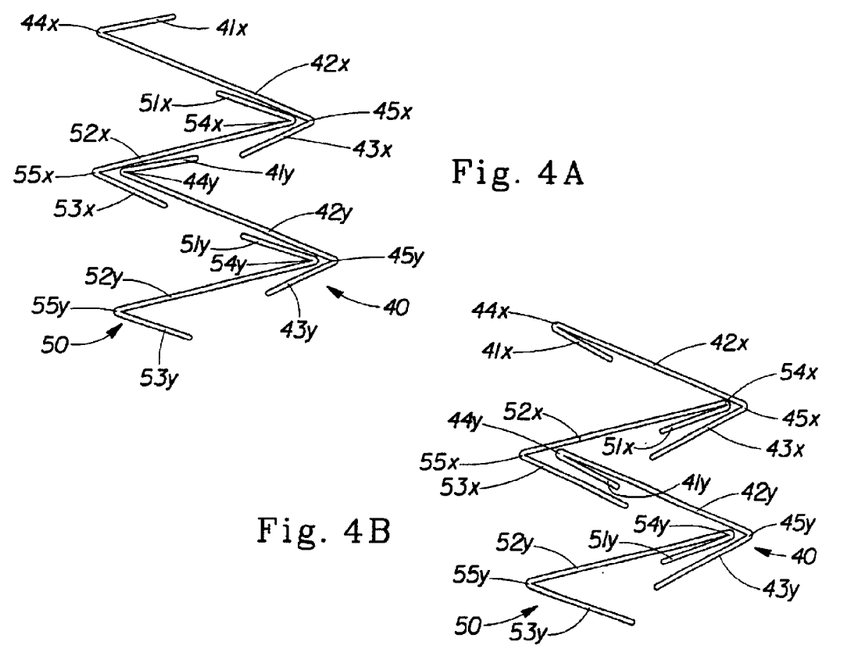
FIGS. 4A–4D are cross-sectional schematic illustrations of folding and interleaving configurations for pre-moistened wet wipes according to a dispensing system of the present invention.

Further in addition to the dispensing improvement, the interleaving configuration of the present invention particularly the embodiment illustrated in FIG. 4A, also ensures that the majority of the substrate material of each wipe in the stack is positioned in the horizontal plane. This reduces the tendency of the stack to produce ridges or grooves of substrate material. Moreover, the stacking configuration also reduces the tendency of the liquid composition to become unevenly distributed throughout the stack.

The further details of the invention will now be described with reference in turn to each of the embodiments 4A, 4B, 4C and 4D.

FIG. 4A, depicts a most preferred stacking configuration of the present invention. The configuration comprises a first assembly of wipes 40 folded in a reversed Z configuration interleaved with a second assembly of wipes folded in a reversed Z fold configuration. Thereby, a portion of the central panel 42x (42y) of each wipe of the first assembly 40 is in contact with a portion of the leading edge panel 51x (51y) of each wipe of the second assembly 50, such that substantially all of one of the surfaces of the leading edge panel 51x (51y) of each of the wipes of the second assembly 50 is in contact with a portion of the central panel 42x (42y) of each of the wipes of the first assembly 40. In this embodiment the leading edge panel 41y and the trailing edge panel 43x (43y) of each of said first assembly of wipes 40 are both no more than 50% the length of said corresponding central panel 42x (42y) and are substantially equal in length. Correspondingly, the leading edge panel 51x (51y) and the trailing edge panel 53x (53y) of each of said second assembly 50 of said wipes are both not more than 50% the length of said corresponding central panel 52x (52y) and are substantially equal in length. Furthermore, the lengths of the leading edge panel 41x (41y), the trailing edge panel 43x (43y) and the central panel 42x (42y) of each of the wipes of the first assembly 40 are substantially equal in length to the lengths of the corresponding leading edge panel 51x (51y), trailing edge panel 53x (53y) and central panel 52x (52y) of the second assembly of wipes 50. In particular, in the embodiment depicted in 4A the leading edge of each of said first assembly of wipes and each of said second assembly of wipes is approximately a quarter of the total length of each of said wipes.

The embodiment depicted in FIG. 4B, is identical to that of 4A in terms of length of the respective panels. However in this embodiment, the wipes of both the first and second assemblies are folded such that the leading edge panel and the trailing edge panel of the wipes is adjacent to the lower surface of the central panel of the corresponding wipe prior to interleaving. Hence, after interfolding according to the present invention, a portion of the central panel 42x (42y) of each wipe of the first assembly 40 is in contact with a portion of the central panel 52x (52y) of each of the wipes of the second assembly 50 and a portion of the tailing edge panel 53x (53y) of the wipes of the second assembly being in contact with the leading edge panel 41y of the wipes of the first assembly 40. Similarly, a portion of the trailing edge panel 53x of each wipe of the second assembly is in contact with a portion of the leading edge panel 41y of each wipe of the first assembly and a portion of the central panel 52x of each wipe of the second assembly is in contact with a portion of the central panel 42y of each wipe of the first assembly of wipes.

Figure 4C:
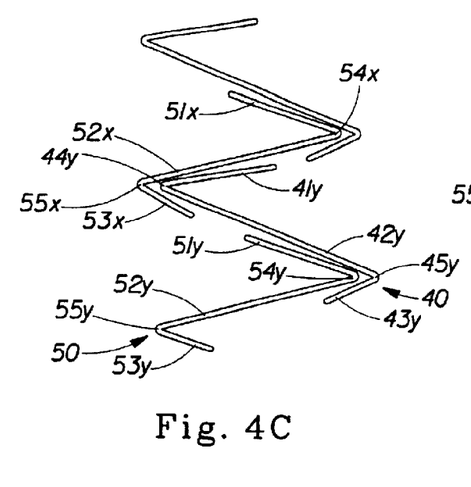
Figure 4D:
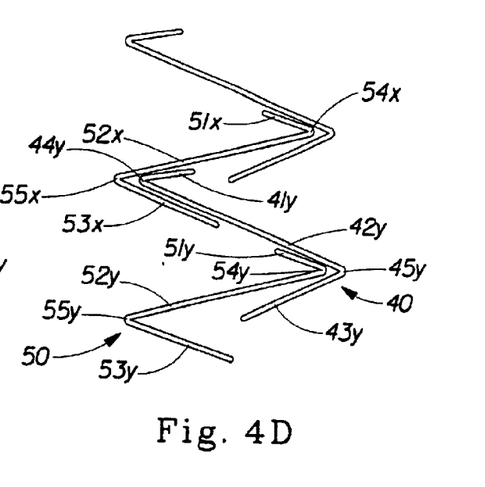

The embodiments according to FIGS. 4C and 4D depict a stacking configuration wherein the wipes of the first assembly 40, are folded in a reversed Z configuration and are interleaved with a second assembly of wipes 50 folded in a Z fold. However in these embodiments the lengths of the leading and trailing edge panel of the wipes of each of the respective assemblies are not equal. In the embodiment depicted in 4C, the length of the leading edge panel of the wipes of both the first and second assemblies is over 50% the length of the central panel and is in fact about 60% the length of the central panel of each of the wipes of both the first and second assemblies. Consequently, the length of the trailing edge panel of each of the wipes of both first and second assemblies is less than 50% of the length of the central panel and is about 30%. In the embodiment depicted in 4D, the length of the trailing edge panel of each of the wipes of both the first and second assemblies is over 50% and is about 60% of the length of the central panel of each of the wipes of both the first and second assemblies. Correspondingly, the length of the leading edge panel of each of the wipes is less than 50%, and is about 30% of the length of the central panel.

In a particularly preferred embodiment according to the present invention, as depicted for example in FIG. 4A, the second panel fold 45x of each of the wipes of the first assembly should not be in direct contact with the first panel fold 54x of each of the adjacent wipes of the second assembly of wipes. Similarly, the second panel fold 55x of each of the wipes of the second assembly should not be in contact with the first panel fold 44y of the adjacent wipes of the first assembly. Preferably, there should be a distance between the fold lines of at least 1 mm, preferably from between 1 mm to 5 mm, and most preferably from between 1 mm and 3 mm. This is because it is believed that contact between two adjacent folds of two adjacent wipes (x of the second and y of the first assemblies) hinders the ability of the uppermost wipe to be separated from the adjacent wipe and cause too much of the substrate material of the adjacent wipe to be separated from the stack.

In another preferred embodiment of the present invention it is also preferable to provide the leading edge or panel with a visual and or tactile indicator. Such indicators further assist in the location of the leading edge itself by the consumer. Visual indicators may be provided' for example in the form of a thin colored strip or band printed on the surface of the leading edge panel in the vicinity of the edge itself.

Of course, as used herein, terms such as "upper" and "lower" are relative terms used in the description above with reference to the FIGURES, with "upper" denoting the portion of the wipe oriented toward the top of the page when read in an upright position. In like manner, however, the stack of interleaved wipes could be inverted, such that the "bottom" of the interleaved stack becomes the "top". As can be appreciated by careful examination of FIGS. 4A–D, such a configuration changes the configuration of the stack. For example, two panels (43y and 53y) are exposed on the uppermost surface of the stack, rather than simply one (41x as shown in FIG. 4A). For certain substrates such a stacked configuration may be more beneficial in providing reliable wipe dispensing.

In a preferred embodiment, the dispensing system of the present invention comprises a container 20 as shown in FIG. 2, the container including a tub portion 21 and a lid 22 pivotably joined to the tub portion. The lid 22 may be removeably attached, and may be attached by a hinge mechanism. In the lid, or more preferably, in an underlying panel or cover 25, the container comprises a dispensing orifice or opening 24. In a preferred embodiment, the cover or lid has a sealing member 27 that serves to help seal a portion of the container when the lid is closed such that drying of the leading of the wipe which is exposed is delayed. Sealing member 27 can be formed in an injection molding process during the manufacture of the container, and may be present on the lid 22 or cover 25 as shown in FIGS. 2 and 5.

Figure 5:
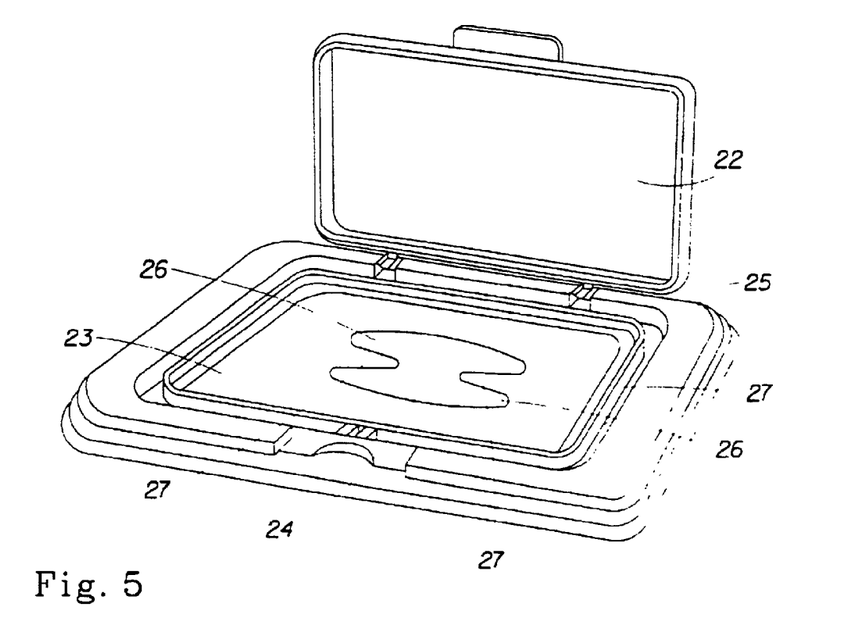
FIG. 5 is a perspective illustration of one embodiment of a cover for a container according to a dispensing system of the present invention.

One embodiment of a lid, cover, and various dispensing openings is shown in FIG. 5. As shown in FIG. 5, a lid 22 can be hingedly attached to a tub cover 25. The dispensing orifice 24 can have wings 27 and inlets 26 formed on the outline edge of the opening. WO 98/19946 is incorporated herein by reference for description of various other opening shapes that can be beneficial in the present invention.

Figure 6:
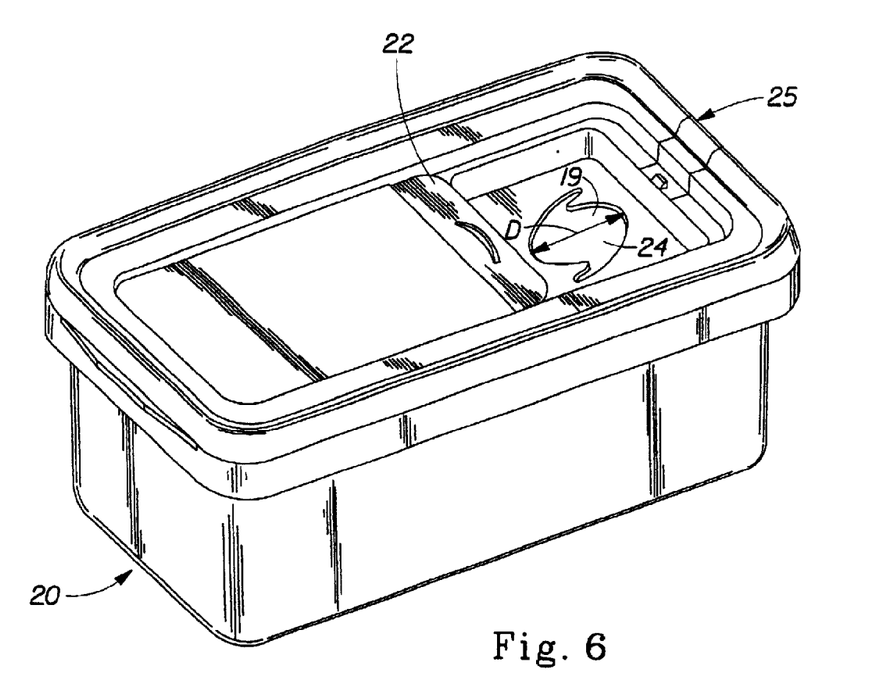
FIG. 6 is a perspective illustration of one embodiment of a container according to a dispensing system of the present invention.

FIG. 6 shows yet another embodiment of a container suitable for the dispensing system of the present invention. In particular, the container 20 shown in FIG. 6 utilizes a sliding lid 22 that covers the opening 24 in cover 25. Also shown in FIG. 6 is a preferred embodiment of the orifice 24 shape. The shape shown, referred to as an S-shaped opening can provide for very reliable pop-up dispensing in all pop-up dispensing systems, including more conventional pop-up tub designs, as shown in FIGS. 2 and 5.

FIG. 6 shows yet another embodiment of a container suitable for the dispensing system of the present invention. In particular, the container 20 shown in FIG. 6 is a preferred embodiment of the orifice 24 in cover 25. Also shown in FIG. 6 is a preferred embodiment of the orifice 24 shape. The shape shown, referred to as an S-shaped opening can provide for very reliable pop-up dispensing in all pop-up dispensing systems, including more conventional pop-up tub designs, as shown in FIGS. 2 and 5. In the preferred pop-up dispensing system of the present invention, an S-shaped opening is used, with the major dimension D of about 54 mm. The overall dimensions of the opening can be modified as needed for beneficial results in dispensing reliability.

SUBSTRATE

The pre-moistened wipe 1 of the present invention comprises a substrate comprising a woven or nonwoven web of natural fibers, synthetic fibers, or mixtures of natural and synthetic fibers. Suitable natural fibers include but are not limited to cellulosic fibers, such as wood pulp fibers, cotton, and rayon. Suitable synthetic fibers include fibers commonly used in textiles, including but not limited to polyester and polypropylene fibers.

Various forming methods can be used to form a suitable fibrous web for use in the present invention. For instance, the web can be made by nonwoven dry forming techniques, such as air-laying, or alternatively by wet laying, such as on a papermaking machine. Other nonwoven manufacturing techniques, including but not limited to techniques such as adhesive bonding, melt blown, spunbonded, needle punched, and hydroentanglement and lamination methods may also be used.

In one embodiment, the dry fibrous web can be an airlaid nonwoven web comprising a combination of natural fibers, staple length synthetic fibers and a latex binder. The dry fibrous web can be about 20–80 percent by weight wood pulp fibers, 10–60 percent by weight staple length polyester fibers, and about 10–25 percent by weight binder.

The dry, fibrous web can have a basis weight of between about 40 and about 80 grams per square meter. The density of the dry web can be measured after evaporating the liquid from the premoistened wipe, and the density can be less than about 0.12 grams per cubic centimeter. The density is the basis weight of the dry web divided by the thickness of the dry web, measured in consistent units, and the thickness of the dry web is measured using a circular load foot having an area of about 2 square inches and which provides a confining pressure of about 95 grams per square inch. In one embodiment, the dry web can have a basis weight of about 64 grams per square meter, a thickness of about 0.06 cm, and a density of about 0.11 grams per cubic centimeter.

In one embodiment, the dry fibrous web can comprise at least 50 percent by weight wood pulp fibers, and more preferably at least about 70 percent by weight wood pulp fibers. One particular airlaid nonwoven web which is suitable for use in the present invention comprises about 73.5 percent by weight cellulosic fibers (Southern softwood Kraft having an average fiber length of about 2.6 mm); about 10.5 percent by weight polyester fibers having a denier of about 1.35 gram/9000 meter of fiber length and a staple length of about 0.85 inch; and about 16 percent by weight of a binder composition comprising a styrene butadiene copolymer. The binder composition can be made using a latex adhesive commercially available as Rovene 5550 (49 percent solids styrene butadiene) available from Mallard Creek Polymers of Charlotte, N.C.

One suitable airlaid nonwoven web for use in the present invention is the airlaid nonwoven web employed in PAMPERS BABY FRESH brand baby wipes marketed by The Procter & Gamble Co. of Cincinnati, Ohio.

The pre-moistened wipe is made by wetting the dry substrate with at least 1 gram of liquid lotion per gram of dry fibrous web. Preferably, the dry substrate is wetted with at least about 2.0, and more preferably at least about 2.5 grams of liquid lotion per gram of the dry fibrous web.

The following patents are incorporated herein by reference for their disclosure related to webs: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; and U.S. Pat. No. 4,637,859; 5,223,096; 5,240,562; 5,556,509; and 5,580,423.

In one alternative embodiment, the substrate can comprise a hydroentangled web having a basis weight of about 62 grams per square meter and comprising about 50 percent by weight rayon fibers and about 50 percent by weight polyester fibers, polypropylene fibers, or a combination thereof. In another alternative embodiment, the substrate can comprise a laminate of two outer hydroentangled webs, such as nonwoven webs of polyester fibers having a basis weight of about 30 grams per square meter, joined to an inner constraining layer, which can be in the form of net-like scrim or a continuous plastic film material which contracts upon heating to provide surface texture in the outer layers.

LOTION

The pre-moistened wipe of the present invention comprises an aqueous solution. The lotion is preferably at least about 85 percent by weight water, more preferably at least about 90 percent by weight water, and still more preferably at least about 95 percent by weight water.

It has been found that phosphate-quaternary amine compounds such as phospholipid surfactants significantly improve the dispensing reliability of pop-up pre-moistened wipes. Without being bound by theory it is believed that phospholipid surfactants reduce adhesional wetting between adjacent wet wipes. Phospholipid-containing surfactants exhibited adequate results as a cleaning solution and as the carrier for other wipe ingredients. However, lotions comprising only phospholipids as the surfactant exhibited negative consumer acceptance due to the relatively poor wetness perception, as compared to commercially available wet wipes.

The lotions of the present invention represent the result of successful attempts to solve the technical contradiction between dispensing reliability and wetness perception in a pre-moistened wipe suitable for reliable pop-up dispensing. Surfactants considered included phospholipid-containing surfactants as one component in the lotion. In general, for most attempts, as wetness perception increased by the addition of additional components such as foam building agents, the dispensing reliability decreased to unacceptable levels. Likewise, as dispensing reliability increased, wetness perception was reduced to unacceptable levels. The lotions of the present invention have been shown to provide an acceptable balance between the two competing characteristics.

By way of example, a panel of 17 consumers were presented with commercially available Pampers® Baby Fresh™ pre-moistened wipes, and asked to compare the wetness perception of those wipes with various embodiments of pre-moistened wipes of the present invention based on the following scale:

+2=much wetter than Pampers® Baby Fresh™ pre-moistened wipes

+1=a little wetter than Pampers® Baby Fresh™ pre-moistened wipes

0=about the same as Pampers® Baby Fresh™ pre-moistened wipes

−1=a little drier than Pampers® Baby Fresh™ pre-moistened wipes

−2=much drier than Pampers® Baby Fresh™ pre-moistened wipes

Pampers® Baby Fresh™ brand of pre-moistened wipes was chosen as the comparison wipe for wetness perception due to its commercial success and consumer acceptance. For each of the lotion samples tested the lotion was applied at levels disclosed herein in a conventional manner to a stack of folded, interleaved wipes, which was then provided to the test panelists in a dispensing container having the S-shaped dispensing orifice disclosed herein. The wipe substrates material used was the same substrate used for Pampers® Baby Fresh™ brand of pre-moistened wipes. Each stack of wipes was aged for approximately one week prior to testing. It has been found that dispensing results change slightly over time, particularly in the first few days following packaging of the wipes into dispensing containers. The results of the panelist's wetness perception test were averaged and are shown below in Table 1. Table 1 Lotion Composition indicates only the ingredients considered critical to the lotion of the present invention, and does not indicate other lotion ingredients such as preservatives and fragrances.

TABLE 1

Comparison of wetness impression of various embodiments to that of Pampers ® Baby Fresh ™ pre-moistened wipes for the top half of a stack of 80 wipes.

| Lotion Composition | Phospholipid surfactant | Block copolymer of propylene oxide and ethylene oxide surfactant | Phospholipid surfactant with ethylene oxide polymer (PEG-7M) | Phospholipid surfactant with alkoxylated alcohol cosurfactant |
|---|---|---|---|---|
| Wetness Rating | −1.7 | −0.7 | −0.3 | −0.2 |

As can be seen in Table 1, the wetness perception of a wipe having a lotion comprising only phospholipid displayed a significant negative score for wetness perception. A score of −1.7 is considered unacceptable for a commercially viable execution of a pre-moistened wet wipe. However, various embodiments of the present invention showed significantly better wetness perception results. These and other various embodiments are described in detail below.

In addition to displaying significantly better wetness perception, it was found that the beneficial dispensing properties certain surfactants alone (e.g., phospholipid surfactants) was maintained to acceptable levels. Thus, dispensing reliability was maintained, while simultaneously delivering a wipe having consumer acceptable wetness perception. By dispensing reliability is meant that the pop-up dispensing failures of chaining, fallbacks, liftoff, and long edges were individually and collectively reduced significantly with use of the lotion of the present invention.

By way of example to illustrate improved reliability, in a Reliability Test 80 Z-folded interleaved wipes using current Pampers® Baby Fresh™ pre-moistened wipes lotion were pulled from a container having the S-shaped opening disclosed herein. Out of the 80 wipes, there were 47 long edges, defined as edges greater than 100 mm extending out of the opening after separation of the pulled wipe, and 37 liftoffs of the tub. By contrast, with all other variables remaining the same, a change to one embodiment of the lotion of the present invention comprising phosphate-quaternary amine compound and non-cellulosic water soluble organic polymers comprising polymers of ethylene oxide resulted in only 23 long edges and 18 liftoffs (out of 80 wipes). This represents a significant improvement in dispensing reliability.

Further reductions in pop-up dispensing failures (and, therefore, increased pop-dispensing reliability), are realized by the synergistic application of the lotions disclosed herein as the present invention, and the folding and interleaving pattern disclosed herein. For example, in the Reliability Test described above, the substrate and lotion of the present invention described above were incorporated into an assymetrical stacked and interleaved Z-folded pattern as disclosed herein. When tested there was only 1 long edge and only 14 liftoffs. This represents a very significant improvement in dispensing reliability.

In particular, having an assymetrical folding pattern substantially as shown in FIG. 4C (but in an inverted position, such that the "bottom" as shown would be the top of the stack in the dispenser) have been found to positively impact dispensing reliability when used with the lotion of the present invention. Without being bound by theory, it is believed that the asymmetrical folding of the panels, e.g., panels 41y and 43y in FIG. 4D, aids in controlling the wipe-to-wipe adhesive forces. Thus, by having one panel having a greater length than the other panel for each wipe (i.e., asymmetrical panel dimensions), the wipe-to-wipe interface is positively impacted to provide for increased dispensing reliability.

The lotion of the present invention comprises an aqueous solution comprising a surfactant selected from the group consisting of phosphate-quaternary amine compounds and non-ionic surfactants, and effective amounts of a second ingredient selected from the group consisting of non-cellulosic organic water soluble polymers and alkoxylated alcohols. These amount of these components can be adjusted in effective amounts to provide varying levels of adhesional wetting to account for various fold patterns and dispensing openings to deliver reliable wet wipe dispensing.

It is believed that the alkoxylated alcohols should be water soluble or water dispersible to facilitate processing the lotion manufacture. It is believed that all combinations of the above mentioned ingredients provide the benefit of reliable pop-up dispensing with adequate wetness impression. Specific non-limiting embodiments are disclosed below.

In one embodiment, the lotion comprises a surfactant comprising phosphate-quaternary amine compounds. Preferred phosphate-quaternary amine compounds include Coco Phosphatidyl PG-Dimonium Chloride, Cocamidopropyl Phosphatidyl PG-Dimonium Chloride, and Stearamidopropyl Phosphatidyl PG-Dimonium Chloride.

A suitable Coco Phosphatidyl PG-Dimonium Chloride is commercially available as Phospholipid CDM-brand of phosphate-quaternary amine surfactant available from Uniqema (formerly Mona Industries, Inc.), Paterson, N.J. A suitable Cocamidopropyl Phosphatidyl PG-Dimonium Chloride is commercially available as Phospholipid PTC from the same supplier. A suitable Stearamidopropyl Phosphatidyl PG-Dimonium Chloride is commercially available as Phospholipid SV from the same supplier.

In one embodiment, the lotion comprises non-cellulosic water soluble organic polymers comprising polymers of ethylene oxide. A preferred polymer is PEG-7M, an ethylene oxide with the formula $H(OCH_2CH_2)_nOH$, and n=150 to 160000. A suitable PEG-7M is commercially available as Polyox WSR N-750 from Union Carbide Corporation, Danbury, Conn. 06817-0001.

In one preferred embodiment, the lotion of the present invention comprises less than about 3 percent by weight of the phosphate-quaternary amine compound and less than about 0.1 percent by weight of the ethylene oxide polymer. In a more preferred embodiment, the lotion can comprise less than about 1 percent by weight of the phosphate-quaternary amine compound and less than about 0.5 percent by weight of the ethylene oxide polymer. Most preferably, the lotion comprises between about 0.28 and about 0.36 percent by weight of the phosphate-quaternary amine compound and between about 0.09 and about 0.11 percent by weight of the ethylene oxide polymer.

In another preferred embodiment, the lotion comprises a phosphate-quaternary amine compound as a surfactant and an alkoxylated alcohol as a cosurfactant. As above, the surfactant can be selected from the group consisting of Coco Phosphatidyl PG-Dimonium Chloride, Cocamidopropyl Phosphatidyl PG-Dimonium Chloride, and Stearamidopropyl Phosphatidyl PG-Dimonium Chloride, each available from the source disclosed above. A suitable alkoxylated alcohol is Isoceteth-20 is commercially available as Arlasolve 200 from Uniqema, Concord Plaza, Wilmington, Del.

The lotion preferably comprises less than about 3 percent by weight of the phosphate-quaternary amine compound and less than about 1 percent by weight of the alkoxylated alcohols. More preferably, the lotion can comprise less than about 1 percent by weight of the phosphate-quaternary amine compound and less than about 0.7 by weight of the alkoxylated alcohols. Still more preferably, the lotion comprises between about 0.28 and about 0.36 percent by weight of the phosphate-quaternary amine compound and between about 0.3 and about 0.5 percent by weight of the alkoxylated alcohols.

In another preferred embodiment, the lotion comprises a nonionic surfactant that is a block copolymer of propylene oxide and ethylene oxide. The propylene oxide block is sandwiched between two ethylene oxide blocks selected from the group consisting of Poloxamer 101- Poloxamer 407. A suitable nonionic surfactant is commercially available as Pluronic 62 brand available from BASF Corporation, Mount Olive, N.J.

The lotion preferably comprises less than about 3 percent by weight of the nonionic surfactant. More preferably, the lotion can comprise less than about 1 percent by weight of the nonionic surfactant. Even more preferably, the lotion comprises between about 0.2 and about 0.3 percent by weight of the nonionic surfactant.

In another preferred embodiment, the lotion comprises an inner salt of fatty quaternaryamines as a surfactant and a sulfonate of a fatty quaternary as a cosurfactant. The surfactant can be selected from the group consisting of Caprylamidopropyl Betaines, Cocoamidopropyl Betaines, Lauramidopropyl Betaine, Oleamidopropyl Bataine, or Isosteramidopropyl Betaine commercially available as Mackam: OAB, 35, L, J, DZ, LMB, and ISA from McIntyre Group Ltd., Governors Highway, University Park, Ill. A suitable cosurfactant is Cocamidopropyl Htdroxysultaine commercially available as Mackam CBS-50G from from McIntyre Group Ltd., Governors Highway, University Park, Ill.

The lotion preferably comprises less than about 3 percent by weight of the inner salt of fatty quaternaryamines and less than about 1 percent by weight of the sulfonate of a fatty quaternary . More preferably, the lotion can comprise less than about 1 percent by weight of the inner salt of fatty quaternaryamines compound and less than about 0.7 by weight of the sulfonate of a fatty quaternary. Still more preferably, the lotion comprises between about 0.15 and about 0.36 percent by weight of the inner salt of fatty quaternaryamines compound and between about 0.1 and about 0.36 percent by weight of the sulfonate of a fatty quaternary.

The lotion preferably also comprises one or more of the following: an effective amount of a preservative, an effective amount of a humectant, an effective amount of an emollient; an effective amount of a fragrance, and an effective amount of a fragrance solubilizer.

As used herein, an emollient is a material that softens, soothes, supples, coats, lubricates, or moisturizes the skin. The term emollient includes, but is not limited to, conventional lipid materials (e.g. fats, waxes), polar lipids (lipids that have been hydrophylically modified to render them more water soluble), silicones, hydrocarbons, and other solvent materials. Emollients useful in the present invention can be petroleum based, fatty acid ester type, alkyl ethoxylate type, fatty acid ester ethoxylates, fatty alcohol type, polysiloxane type, mucopolysaccharides, or mixtures thereof.

Humectants are hygroscopic materials that function to draw water into the stratum corneum to hydrate the skin. The water may come from the dermis or from the atmosphere. Examples of humectants include glycerin, propylene glycol, and phospholipids.

Fragrance components, such as perfumes, include, but are not limited to water insoluble oils, including essential oils.

Fragrance solubilizers are components which reduce the tendency of the water insoluble fragrance component to precipitate from the lotion. Examples of fragrance solubilizers include alcohols such as ethanol, isopropanol, benzyl alcohol, and phenoxyethanol; any high HLB (HLB greater than 13) emulsifier, including but not limited to polysorbate; and highly ethoxylated acids and alcohols.

Preservatives prevent the growth of micro-organisms in the liquid lotion and/or the substrate. Generally, such preservatives are hydrophobic or hydrophilic organic molecules. Suitable preservatives include, but are not limited to parabens, such as methyl parabens, propyl parabens, and combinations thereof.

The lotion can also comprise an effective amount of a kerotolytic for providing the function of encouraging healing of the skin. An especially preferred kerotolytic is Allantoin ((2,5-Dioxo-4-Imidazolidinyl)Urea), a heterocyclic organic compound having an empirical formula $C_4H_6N_4O_3$. Allantoin is commercially available from Tri-K Industries of Emerson, N.J. It is well recognized that the long term wear of disposable absorbent structures, such as disposable diapers, may lead to skin which is compromised in terms of being over hydrated. It is generally known that hyperhydrated skin is more susceptible to skin disorders, including heat rash, abrasion, pressure marks and skin barrier loss. For example, 21 CFR 333.503 defines diaper rash as an inflammatory skin condition in the diaper area (perineum, buttocks, lower abdomen, and inner thighs) caused by one or more of the following factors: moisture, occlusion, chafing, continued contact with urine or feces, or mechanical or chemical irritation. A premoistened wipe according to the present invention can include an effective amount of allantoin for encouraging the healing of skin, such as skin which is over hydrated.

U.S. Pat. No. 5,534,265 issued Jul. 9, 1996; U.S. Pat. No. 5,043,155 issued Aug. 27, 1991; and U.S. Pat. No. 5,648,083 issued Jul. 15, 1997 are incorporated herein by reference for the purpose of disclosing additional lotion ingredients.

One suitable lotion of the present invention comprises at least 95 percent by weight water, between about 0.12 to about 0.6 percent by weight Coco Phosphatidyl PG-Dimonium Chloride or 0.15 percent by weight to 0.5 percent by weight Poloxamer 182, which can serve as a surfactant; between about 0.5 to about 5 percent by weight propylene glycol, which can serve as a humectant; between about 0.1 to about 1 percent by weight Isoceteth-20 or Polysorbate 20, which can serve as an emulsifier for solubilizing fragrance components; about 0.01 to about 0.5 percent by weight Methylparaben, which can serve as a preservative; about 0.01 to about 0.1 percent by weight Propylparaben, which can serve as a preservative; about 0.01 to about 0.1 percent by weight 2-Bromo-2-Nitropropane-1, 3-Diol which can serve as a preservative; between 0.05% to 0.3% PEG-7m, which can serve as a foam builder; and about 0.01 to about 1 percent by weight of one or more fragrance components.

The lotion can further comprise between about 0.1 and about 3 percent by weight Allantoin, and about 0.1 to about 10 percent by weight of an aloe extract, such as aloe vera, which can serve as an emollient. Aloe vera extract is available in the form of a concentrated powder from the Rita Corporation of Woodstock, Ill.

The phosphate-quaternary amine compound or nonionic surfactant provides effective yet gentle cleaning. It is also believed that the alkoxylated alcohols or phosphate-quaternary amine compound provides secondary solubilization of the fragrance oils in the aqueous lotion.

The lotion of the present invention can be made according to the Examples which follow, which Examples are meant to be exemplary and not limiting.

EXAMPLE 1

A suitable lotion for use in a pre-moistened baby wipe can be made according to the following steps to provide a 500 gram batch:

1. 0.5 grams of Polyox WSR N-750 is added to 250 grams of deionized water, with agitation.
2. A first premix (premix A) is prepared by mixing together:
   A. 7.50 grams of propylene glycol (liquid), which serves as a solvent/humectant; and
   B. 1.15 grams of Methyl/Propyl Paraben (powder), which serves as preservative.
3. A second premix (premix B) is prepared by mixing together:

A. 1.00 grams of Polysorbate 20 (liquid), which serves as a fragrance solubilizer; and
B. 0.19 grams of fragrance oil (liquid).
4. Premix B is then added to the Polyox WSR N-750 and 250 grams of deionized water, with agitation.
5. 0.25 grams of Bronopol is then added to the mixture of step 4. The Bronopol (2-bromo-2-nitropropane-1,3-diol) (powder) serves as a preservative.
6. 4.5 grams of Phospholipid CDM liquid (40 percent by weight phosphate-quaternary amine compound is then added to the mixture of step 5.
7. 2.5 grams of Allantoin solids (powder) is then added to the mixture of step 6.
8. Sufficient deionized water is then added to the mixture of step 7 to q.s. to 100 percent.
9. Premix A is then added to the mixture of step 8, with agitation.

The lotion made according to the above example comprises about 0.1 percent by weight nonionic polymer, 0.36% phosphate-quaternary amine compound, and about 0.5 percent by weight Allantoin.

EXAMPLE 2

A lotion according to this example is made as described above for Example 1, with the following modification. Prior to adding sufficient deionized water to q.s. to 100 percent, 0.0125 grams of a concentrated aloe vera extract powder (200 to 1 concentration) is added to the mixture. The resulting lotion comprises about 0.5 percent by weight aloe vera extract.

EXAMPLE 3

A suitable lotion for use in a pre-moistened wipe can be made according to the following example to provide a 500 gram batch:
1. A first premix (premix A) is prepared by mixing together:
    A. 7.50 grams of propylene glycol (liquid), which serves as a solvent/humectant; and
    B. 1.15 grams of Methyl/Propyl Paraben (powder), which serves as preservative.
2. A second premix (premix B) is prepared by mixing together:
    A. 1.50 grams of Phospholipid CDM (liquid-40 percent by weight phosphate-quaternary amine compound solids); and
    B. 0.19 grams of fragrance oil (liquid).
3. Premix B is then added to 250 grams of deionized water, with agitation.
4. 0.25 grams of Bronopol is then added to the mixture of step 3. The Bronopol (2-bromo-2-nitropropane-1,3-diol) (powder) serves as a preservative.
5. 3.0 grams of Phospholipid CDM liquid (40 percent by weight phosphate-quaternary amine compound is then added to the mixture of step 4.
6. 2.0 grams of Arlasolve 200 is then added to the mixture of step 5.
7. 2.5 grams of Allantoin solids (powder) is then added to the mixture of step 6.
8. Sufficient deionized water is then added to the mixture of step 7 to q.s. to 100 percent.
9. Premix A is then added to the of step 8 mixture, with agitation.

The lotion made according to the above example comprises about 0.4 percent by weight Isoceteth-20, 0.32% phosphate-quaternary amine compound, and about 0.5 percent by weight Allantoin.

EXAMPLE 4

A suitable lotion for a pre-moistened wipe comprising a nonionic surfactant that is a block copolymer of propylene oxide and ethylene oxide can be made according to the following example to provide a 500 gram batch:
1. A first premix (premix A) is prepared by mixing together:
    A. 7.50 grams of propylene glycol (liquid), which serves as a solvent/humectant; and
    B. 1.15 grams of Methyl/Propyl Paraben (powder), which serves as preservative.
2. A second premix (premix B) is prepared by mixing together:
    A. 1.0 grams of Polysorbate 20, which serves as a fragrance solubilizer;
    B. 0.19 grams of fragrance oil (liquid).
3. Premix B is then added to 250 grams of deionized water, with agitation.
4. 0.25 grams of Bronopol is then added to the mixture of step 3. The Bronopol (2-bromo-2-nitropropane-1,3-diol) (powder) serves as a preservative.
5. 2.5 grams of Pluronic 62 liquid (50 percent by weight a nonionic surfactant that is a block copolymer of propylene oxide and ethylene oxide solids) is then added to the mixture of step 4.
6. 2.5 grams of Allantoin solids (powder) is then added to the mixture of step 5.
7. Sufficient deionized water is then added to the mixture of step 6 to q.s. to 100 percent.
8. Premix A is then added to the mixture of step 7, with agitation.

The lotion made according to the above example comprises about 0.125 percent by weight Pluronic 62 nonionic surfactant that is a block copolymer of propylene oxide and ethylene oxide, and about 0.5 percent by weight Allantoin.

EXAMPLE 5

A suitable lotion for a pre-moistened wipe comprising a nonionic surfactant that is a block copolymer of propylene oxide and ethylene oxide can be made according to the following example to provide a 500 gram batch:
1. A first premix (premix A) is prepared by mixing together:
    A. 7.50 grams of propylene glycol (liquid), which serves as a solvent/humectant; and
    B. 1.15 grams of Methyl/Propyl Paraben (powder), which serves as preservative.
2. A second premix (premix B) is prepared by mixing together:
    A. 2.0 grams of Cocamidopropyl Betaine(liquid), which serves as a fragrance solubilizer and surfactant;
    B. 0.19 grams of fragrance oil (liquid).
3. Premix B is then added to 250 grams of deionized water, with agitation.
4. A third premix (premix c) is prepared by mixing together:
    A. 1.5 grams of Cocamidopropyl Hydroxysulatine, which serves as a solubilizer and cosurfactant;
    B. 0.25 grams of Dimethicone copolyol (liquid).
5. Premix B is then added to 250 grams of deionized water, with agitation.

6. 0.25 grams of Bronopol is then added to the mixture of step 3. The Bronopol (2-bromo-2-nitropropane-1,3-diol) (powder) serves as a preservative.

7. 2.5 grams of Allantoin solids (powder) is then added to the mixture of step 5.

8. Sufficient deionized water is then added to the mixture of step 6 to q.s. to 100 percent.

9. Premix A is then added to the mixture of step 7, with agitation.

The lotion made according to the above example comprises about 0.16 percent by weight Mackam LMB surfactant that is an inner salt of fatty quaternaryamines, 0.12% Mackam CBS 50-G that is a sulfonate of a fatty quaternary, and about 0.5 percent by weight Allantoin.

Accordingly, while particular embodiments of the present invention have been illustrated and described, it would be obvious to those skilled in the art that various other changes and modifications can be made without departing from the spirit and scope of the invention. It is therefore intended to cover in the appended claims all such changes and modifications, including combinations of features disclosed, that are within the scope of this invention.

What is claimed is:

1. A pop-up dispensing system for reliable single dispensing of discreet pre-moistened wipes in consecutive order, the system comprising:
   (a) a container having an interior portion and an aperture for drawing through the pre-moistened wet wipes in consecutive order;
   (b) a plurality of the pre-moistened wipes, the wipes being stacked, folded and interleaved in a substantially interfolded z-fold pattern in the interior portion of the container;
   wherein the pre-moistened wipes are wetted with a lotion, the lotion being an aqueous solution comprising at least about 90% by weight water, a surfactant selected from the group consisting of phosphate-quaternary amine compounds and non-ionic surfactants, and effective amounts of a second ingredient selected from the group consisting of non-cellulosic organic water soluble polymers and alkoxylated alcohols and wherein each of the pre-moistened wipes has a leading edge panel having a length of from about 2 cm to about 7 cm, a central panel having a length of from about 3 cm to about 12 cm, and a trailing edge panel having a length of from about 2 cm to about 7 cm and wherein the phosphate-quaternary amine compound is selected from the group consisting of Coco Phosphatidyl PG-Dimonium Chloride, Cocamidopropyl Phosphatidyl PG-Dimonium Chloride, and Stearamidopropyl Phosphatidyl PG-Dimonium Chloride.

2. The pop-up dispensing system of claim 1 wherein the lotion comprises less than about 3 percent by weight of the phosphate-quaternary amine compound.

3. A pop-up dispensing system for reliable single dispensing of discreet pre-moistened wipes in consecutive order, the system comprising:
   (a) a container having an interior portion and an aperture for drawing through the pre-moistened wet wipes in consecutive order;
   (b) a plurality of the pre-moistened wipes, the wipes being stacked, folded and interleaved in a substantially interfolded z-fold pattern in the interior portion of the container;
   wherein the pre-moistened wipes are wetted with a lotion, the lotion being an aqueous solution comprising at least about 90% by weight water, a surfactant selected from the group consisting of phosphate-quaternary amine compounds and non-ionic surfactants, and effective amounts of a second ingredient selected from the group consisting of non-cellulosic organic water soluble polymers and alkoxylated alcohols and wherein each of the pre-moistened wipes has a leading edge panel having a length of from about 2 cm to about 7 cm, a central panel having a length of from about 3 cm to about 12 cm, and a trailing edge panel having a length of form about 2 cm to about 7 cm and further comprising an effective amount of a fragrance and an effective amount of a fragrance solublizer.

4. A pop-up dispensing system for reliable single dispensing of discreet pre-moistened wipes in consecutive order, the system comprising:
   (a) a container having an interior portion and an aperture for drawing through the pre-moistened wet wipes in consecutive order;
   (b) a plurality of the pre-moistened wipes, the wipes being stacked, folded and interleaved in a substantially interfolded z-fold pattern in the interior portion of the container;
   wherein the pre-moistened wipes are wetted with a lotion, the lotion being an aqueous solution comprising at least about 90% by weight water, a surfactant selected from the group consisting of phosphate-quaternary amine compounds and non-ionic surfactants, and effective amounts of a second ingredient selected from the group consisting of non-cellulosic organic water soluble polymers and alkoxylated alcohols and wherein each of the pre-moistened wipes has a leading edge panel having a length of from about 2 cm about 7 cm, a central panel having a length of from about 3 cm to about 12 cm, and a trailing edge panel having a length of from about 2 cm to about 7 cm and further comprising a kertolytic.

5. The pop-ip dispensing system of claim 4 wherein the kerotolytic comprises allantoin.

6. A pop-up dispensing system for reliable single dispensing of discreet pre-moistened wipes in consecutive order, the system comprising:
   (a) a container having an interior portion and an aperture for drawing through the pre-moistened wet wipes in consecutive order;
   (b) a plurality of the pre-moistened wipes, the wipes being stacked, folded and interleaved in a substantially interfolded z-fold pattern in the interior portion of the container;
   wherein the pre-moistened wipes are wetted with a lotion, the lotion being an aqueous solution comprising at least about 90% by weight water, a surfactant selected from the group consisting of phosphate-quaternary amine compounds and non-ionic surfactants, and effective amounts of a second ingredient selected from the group consisting of non-cellulosic organic water soluble polymers and alkoxylated alcohols and wherein each of the pre-moistened wipes has a leading edge panel having a length of from about 2 cm to about 7 cm, a central panel having a length of from about 3 cm to about 12 cm, and a trailing edge panel having a length of from about 2 cm to about 7 cm wherein the pre-moistened wipes comprise a nonwoven substrate and wherein the substrate is wetted with at least 1.0 gram of the lotion per gram of dry substrate weight.

7. The pop-up dispensing system of claim 6 wherein the substrate is wetted with at least 2.0 gram of the lotion per gram of dry substrate weight.

* * * * *

UNITED STATES PATENT AND TRADEMARK OFFICE
CERTIFICATE OF CORRECTION

PATENT NO. : 6,960,349 B2
DATED : November 1, 2005
INVENTOR(S) : Schantz et al.

It is certified that error appears in the above-identified patent and that said Letters Patent is hereby corrected as shown below:

Column 10,
Delete lines 12-19 entirely.
Line 20, delete "as shown in Figs. 2 and 5."

Column 12,
Table 1, heading of the $3^{rd}$ column, $2^{nd}$ line, before "propylene" delete "of".

Column 20,
Line 9, delete "form" and insert -- from --.
Line 32, after "2 cm" insert -- to --.
Line 35, delete "kertolytic" and insert -- kerotolytic --.
Line 36, delete "pop-ip" and insert -- pop-up --.

Signed and Sealed this

Twenty-first Day of February, 2006

JON W. DUDAS
*Director of the United States Patent and Trademark Office*